(12) United States Patent
Feiertag et al.

(10) Patent No.: US 9,155,593 B2
(45) Date of Patent: *Oct. 13, 2015

(54) POSITIONING UNIT AND MONITORING DEVICE

(75) Inventors: Carsten Feiertag, Hungen (DE);
Guenter Pfeiffer, Gladenbach (DE);
Rainer Kirchhuebel, Asslar (DE)

(73) Assignee: Oculus Optikgeraete GmbH, Wetzlar-Dutenhofen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/354,841

(22) Filed: Jan. 20, 2012

(65) Prior Publication Data

US 2012/0327370 A1 Dec. 27, 2012

(30) Foreign Application Priority Data

Jan. 20, 2011 (DE) .......................... 10 2011 002 941

(51) Int. Cl.
*A61B 3/10* (2006.01)
*A61B 19/00* (2006.01)
(Continued)

(52) U.S. Cl.
CPC .............. *A61B 19/26* (2013.01); *A61B 3/0075* (2013.01); *G02B 7/001* (2013.01); *G02B 7/021* (2013.01);
(Continued)

(58) Field of Classification Search
CPC ............... A61B 19/26; A61B 19/5223; A61B 2019/265; G02B 7/001; G02B 21/0012; F21V 21/00
USPC .......... 351/205, 216, 246, 261; 359/368, 381, 359/382; 606/4–6
See application file for complete search history.

(56) References Cited

U.S. PATENT DOCUMENTS 3,881,810 A    5/1975    Colao
4,095,874 A *   6/1978    Wallace ........................ 359/804

(Continued)

FOREIGN PATENT DOCUMENTS

CN    101346104 A    1/2009
CN    100471721 C    3/2009

(Continued)

OTHER PUBLICATIONS

European Search Report issued in related application 12150154.8, completed Jul. 19, 2012 and mailed Jul. 30, 2012.

(Continued)

*Primary Examiner* — Thomas K Pham
*Assistant Examiner* — Cara Rakowski
(74) *Attorney, Agent, or Firm* — Griffin & Szipl, P.C.

(57) ABSTRACT

A positioning unit (11) for positioning an optical unit (12, 13) comprising at least one optical element in a beam path (20) of a microscope between an objective lens of a microscope and in front of an eye to be monitored is provided, wherein the positioning unit comprises a connection device (21), by means of which the positioning unit can be coupled to the microscope, wherein the positioning unit comprises a positioning device (22), by means of which the optical element is movable relative to the microscope in the longitudinal direction of the beam path, wherein the positioning device is formed by a first double rocker mechanism (31) and a second double rocker mechanism (32), wherein the double rocker mechanisms are interconnected by means of a common coupling member (33). A monitoring device (10) is also provided that comprises the positioning unit (11).

18 Claims, 5 Drawing Sheets

(51) Int. Cl.
  *A61B 3/00* (2006.01)
  *G02B 7/00* (2006.01)
  *G02B 7/02* (2006.01)
  *G02B 21/00* (2006.01)

(52) U.S. Cl.
  CPC ............ *G02B 7/023* (2013.01); *G02B 21/0012* (2013.01); *A61B 19/5223* (2013.01); *A61B 2019/265* (2013.01)

(56) References Cited

U.S. PATENT DOCUMENTS

| | | | |
|---|---|---|---|
| 6,215,081 B1 * | 4/2001 | Jensen et al. | 200/341 |
| 6,550,734 B1 * | 4/2003 | Spadea | 248/280.11 |
| 6,901,774 B2 * | 6/2005 | Maeda | 65/348 |
| 7,886,903 B1 * | 2/2011 | Wurzelbacher et al. | 206/320 |
| 2004/0184142 A1 | 9/2004 | Akiyama et al. | |
| 2004/0232283 A1 * | 11/2004 | Ferry et al. | 244/118.6 |
| 2005/0225848 A1 | 10/2005 | Kirchhuebel | |
| 2006/0291044 A1 * | 12/2006 | Nozawa et al. | 359/382 |
| 2007/0173756 A1 | 7/2007 | Krebs et al. | |
| 2008/0084540 A1 | 4/2008 | Gaida | |
| 2009/0219483 A1 | 9/2009 | Takanashi et al. | |
| 2009/0237814 A1 | 9/2009 | Feiertag et al. | |
| 2010/0265460 A1 | 10/2010 | Mann | |

FOREIGN PATENT DOCUMENTS

| | | |
|---|---|---|
| CN | 102599881 A | 7/2012 |
| DE | 41 16 810 A1 | 11/1992 |
| DE | 4116810 A1 | 11/1992 |
| DE | 202 15 635 U1 | 12/2002 |
| DE | 103 36 893 A1 | 5/2004 |
| DE | 60 2004 006178 T2 | 12/2007 |
| DE | 10 2006 047459 A1 | 4/2008 |
| DE | 20 2008 004 018 U1 | 6/2008 |
| DE | 10 2008 011608 A1 | 9/2009 |
| DE | 10 2009 018114 A1 | 1/2011 |
| JP | 2001046399 A | 2/2001 |
| JP | 2001112777 A | 4/2001 |
| JP | 2004133461 A | 4/2004 |
| JP | 2005312529 A | 11/2005 |
| JP | 2006102155 A | 4/2006 |
| JP | 2008501378 A | 1/2008 |
| JP | 2009205156 A | 9/2009 |

OTHER PUBLICATIONS

Search report issued in related European application 12150154, completed Apr. 4, 2012 and mailed Apr. 12, 2012 (no translation available).
Search report issued in corresponding European application 12150156, completed Apr. 4, 2012 and mailed Apr. 18, 2012 (no translation available).
English Translation of issued Japanese Office Action in related matter No. 2012-006643, drafted Jul. 17, 2013 and dispatched Jul. 19, 2013.
English Translation of issued Japanese Office Action in related matter No. 2012-006642, drafted Jul. 17, 2013 and dispatched Jul. 19, 2013.
Office Action issued in pending related U.S. Appl. No. 13/354,743 mailed on Jul. 30, 2013.
English Translation of Chinese Office Action in parallel Chinese application 2012100168291, dated Dec. 23, 2013.
English Translation of Japanese Office Action in parallel Japanese application 2012-006643, completed Feb. 3, 2014 and mailed on Feb. 6, 2014.
English Translation of Chinese Office Action in parallel Chinese application 201210017914.X, completed Feb. 8, 2014 and mailed Mar. 7, 2014.

* cited by examiner

POSITIONING UNIT AND MONITORING DEVICE

This application claims priority from German Patent Application No. DE 10 2011 002 941.9, filed Jan. 20, 2011, the entire disclosure of which is incorporated herein by reference.

FIELD OF THE INVENTION

The invention relates to a positioning unit for positioning an optical unit comprising at least one optical element in a beam path of a microscope between an objective lens of a microscope and in front of an eye to be monitored, wherein the positioning unit comprises a connection device by means of which the positioning unit can be coupled to the microscope, wherein the positioning unit comprises a positioning device, by means of which the optical element is movable relative to the microscope in the longitudinal direction of the beam path. The invention also relates to a monitoring device comprising such a positioning unit.

BACKGROUND OF THE INVENTION

Microscopes for carrying out eye operations are regularly used for operations in a front area of an eye. Should such interventions be undertaken in a rear area of an eye, it is necessary to supplement the microscope with a monitoring device, which makes it possible to focus on precisely this area of the eye. Such monitoring devices comprise at least one wide angle lens, or ophthalmoscopy lens, for wide-angle examination of the relevant rear part of the eye, wherein the ophthalmoscopy lens provides an intermediate image in a beam path in front of an objective lens of the microscope. This intermediate image cannot be focused with the microscope. Depending on the focal length of the auxiliary optics and of the examined eye, the intermediate image appears sharp in a position that lies closer to the object. To focus the intermediate image, it is necessary to shorten the focal length of the microscope object. A height adjustment of the microscope does not change the focal length. By using a reducing lens in the beam path beneath the microscope object, the plane of the intermediate image may lie in the focus of the microscope. In order to focus this intermediate image using the microscope, the microscope has to be moved or spaced in relation to the ophthalmoscopy lens over a distance. This change in height is basically determined by the individual refractive power of the eye, and by the different refractive power(s) of the selected ophthalmoscopy lens.

The two lenses are held by a positioning unit of the monitoring device, which is fixed directly on the microscope, and, if necessary, they can be positioned in the beam path without the need for considerable adjustment of the microscope during an operation. The positioning unit generally comprises a connection device, by means of which the positioning unit can be coupled to the microscope. The positioning unit is also formed in such a way that the relevant lens can be easily pivoted or slid into the beam path and removed therefrom again.

In order to adapt the intermediate image of the ophthalmoscopy lens, as precisely as possible, to a focal length of the microscope objective lens, at least one of the lenses is designed to be adjustable along the beam path of the microscope. In known monitoring devices, a linear guide is provided on the positioning unit, for example, for adjustment of the lens in a longitudinally displaceable manner, wherein the lens can be moved by means of an adjusting wheel having a screw drive. In order to prevent an accidental collision between the ophthalmoscopy lens and the eye, or to avoid possible damage to the eye during an operation, the positioning unit is formed in such a way that the ophthalmoscopy lens is movable, essentially without resistance, in the direction of the objective lens of the microscope, that is to say, it can move back in the event of a collision with the eye. For example, this is achieved by a second linear guide that also enables a longitudinal displacement of the ophthalmoscopy lens.

In addition to the above-described mechanical and optical requirements, it is important that the monitoring device and the positioning unit are basically sterile during an operation, so as to prevent a possible infection of an eye with germs, for example. In particular, there is a risk of infection since the monitoring device is advanced relatively tightly against the eye in question during an operation. The possibility of an infection of the patient's eye by an insufficiently prepared positioning unit is ruled out by use of a disposable positioning unit, supplied in a sterile state. It is therefore usual to sterilise the monitoring device and positioning unit in question before an operation, for example, by steam sterilisation. To carry out repeated sterilisation, it is absolutely necessary to form all components of the monitoring device and positioning unit, except for any seals made of resilient materials such as rubber, from metal or glass. Other materials, such as plastics materials, have not proven to be very durable for repeated sterilisation. The linear guides and the screw drive also have to be formed in a dimensionally accurate manner to ensure specific fits, and, therefore, only components made of metal are also considered in this instance. To prevent an infiltration of water into the guides during the sterilisation, these can be provided with rubber seals, or seals made of other resilient materials. It is also necessary to lubricate corresponding pairs of sliding surfaces of the guides, and of the screw drive, at regular intervals using a lubricant so as to ensure the function thereof.

The monitoring devices and positioning units known from the prior art pose a range of drawbacks. A weight of the monitoring device, which can be adapted, for example, to an adapter plate on the microscope screwed onto the microscope, is, therefore, relatively high and disruptive in the event of handling of the monitoring device during an operation. The linear guides can also only be sealed or sterilised with difficulty. During steam sterilisation, water or steam can only infiltrate the screw paths of the screw drive with difficulty, and, therefore, undesired water residues or germs may still remain in the screw paths after the steam sterilisation. It is also disruptive that the lubricants used are removed, at least in part, during the steam sterilisation and contaminate the water used for sterilisation. The sterilisation process itself is also to be considered problematic since it cannot be ruled out with absolute certainty that germs will still remain on the monitoring device and on the positioning unit after the steam sterilisation. The quality of a sterilisation process is, therefore, also dependent, inter alia, on water quality in a steam sterilisation apparatus.

Furthermore, a monitoring device and a positioning unit are to be sterilised after each use, and, therefore, the monitoring device and positioning unit cannot be used directly after use in subsequent eye operations owing to the sterilisation times. As the case may be, it is necessary to obtain and have available a plurality of monitoring devices and positioning units so that operations can be carried out without any time restraint. High overall costs for production, sterilisation, and maintenance of the monitoring device and positioning unit are thus sustained by a user, as well as costs incurred owing to increased capital investment.

The object of the present invention is, therefore, to propose a positioning unit and a monitoring device that comprises a movement mechanism that is easier to clean.

SUMMARY OF THE INVENTION

This object of the invention is achieved by a positioning unit having the features according to a first embodiment, and to a monitoring device having the features according to a sixteenth embodiment. More specifically, in accordance with the first embodiment of the present invention, a positioning unit (11, 60) for positioning an optical unit (12, 13) that comprises at least one optical element in a beam path (20) of a microscope between an objective lens of the microscope and in front of an eye to be monitored, wherein the positioning unit comprises: (a) a connection device (21, 61), by means of which the positioning unit can be coupled to the microscope; and the positioning unit further comprising (b) a positioning device (22), by means of which the optical element is movable relative to the microscope in the longitudinal direction of the beam path, characterised in that the positioning device is formed of a first double rocker mechanism (31, 64) and a second double rocker mechanism (32, 65), wherein the double rocker mechanisms are interconnected by means of a common coupling member (33, 72). In accordance with a second embodiment of the present invention, the first embodiment is modified so that the positioning unit (11, 60) is formed, at least in part, of plastics material. In accordance with a third embodiment of the present invention, either the first embodiment or the second embodiment are further modified so that the first double rocker mechanism (31, 64) is connected to the second double rocker mechanism (32, 65) via a toothed gearing (43, 72) in such a way that a movement of the first double rocker mechanism is transferable to the second double rocker mechanism.

In accordance with a fourth embodiment of the present invention, the third embodiment is further modified so that the double rocker mechanisms (31, 32) and the toothed gearing (43) are formed together in one piece. In accordance with a fifth embodiment of the present invention, the third embodiment and the fourth embodiment are further modified so that the toothed gearing (43, 77) has a gear ratio of 1:1. In accordance with a sixth embodiment of the present invention, the first embodiment, the second embodiment, the third embodiment, the fourth embodiment and the fifth embodiment are further modified so that a first double rocker of the first double rocker mechanism (31, 64) is mounted on a connecting bearing member (37, 66), and a second double rocker of the second double rocker mechanism (32, 65) is mounted on a receiving bearing member (40, 74).

In accordance with a seventh embodiment of the present invention, the first embodiment, the second embodiment, the third embodiment, the fourth embodiment, the fifth embodiment, and the sixth embodiment, are further modified so that the positioning device (22) comprises an adjustment means (46), by means of which a position of the optical element is adjustable. In accordance with an eighth embodiment of the present invention, the seventh embodiment is further modified so that the adjustment means (46) is formed of at least one adjusting wheel (40, 52, 67) having a worm gear or an eccentric gear (51). In accordance with a ninth embodiment of the present invention, the first embodiment, the second embodiment, the third embodiment, the fourth embodiment, the fifth embodiment, the sixth embodiment, the seventh embodiment, and the eighth embodiment, are further modified so that the positioning device (22) forms a safety means (56) that allows a loose movement of the optical element if a force is exerted on the optical element in the direction of the microscope.

In accordance with a tenth embodiment of the present invention, the first embodiment, the second embodiment, the third embodiment, the fourth embodiment, the fifth embodiment, the sixth embodiment, the seventh embodiment, the eighth embodiment, and the ninth embodiment, are further modified so that the positioning unit (11) comprises an alternating device (23), by means of which the optical element can be moved into and out of the beam path (20). In accordance with an eleventh embodiment of the present invention, the tenth embodiment is further modified so that the alternating device (23) is formed by the connection device (21) and the positioning device (22) in such a way that the positioning device is pivotable relative to the connection device. In accordance with a twelfth embodiment of the present invention, the tenth embodiment and the eleventh embodiment are further modified so that the alternating device (23) is formed as a hinge, the alternating device comprising at least one snap-in means (28, 29), by means of which the optical element is lockable in a use position in the beam path (22) and/or in an idle position outside the beam path. In accordance with a thirteenth embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment and the twelfth embodiment, are further modified so that link brackets of the double rocker mechanisms (31, 32) are formed in each case by a living hinge (36). In accordance with a fourteenth embodiment of the present invention, the first embodiment, the second embodiment, the third embodiment, the fourth embodiment, the fifth embodiment, the sixth embodiment, the seventh embodiment, the eighth embodiment, the ninth embodiment, the tenth embodiment, the eleventh embodiment, the twelfth embodiment and the thirteenth embodiment are further modified so that the positioning unit (11) is formed completely of plastics material.

In accordance with a fifteenth embodiment of the present invention, a monitoring device (10, 59) is provided that comprises (i) a positioning unit (11, 60) according to any one of the first embodiment, the second embodiment, the third embodiment, the fourth embodiment, the fifth embodiment, the sixth embodiment, the seventh embodiment, the eighth embodiment, the ninth embodiment, and the tenth embodiment; and (i) at least one optical unit (12, 13), wherein the optical unit comprises at least one optical element. In accordance with a sixteenth embodiment of the present invention, the fifteenth embodiment is modified so that the positioning unit (11, 60) further comprises a receiving device (19, 55, 63), by means of which the optical unit can be adapted to the positioning unit, wherein the optical unit forms a holding means (16) for holding the optical element and connecting it to the receiving device. In accordance with a seventeenth embodiment of the invention, the fifteenth embodiment is further modified so that the positioning unit (60) forms a holding means (62) for holding the optical element. In accordance with an eighteenth embodiment of the invention, the sixteenth embodiment and the seventeenth embodiment are further modified so that the holding means (16) and/or the receiving device (19, 55, 63) and/or a connection device (21, 61) comprises at least one connecting element (57), which is formed in such a way that it is destroyed upon separation of the holding means and the receiving device and/or the connection device and a microscope.

The positioning unit, according to the invention, for positioning an optical unit comprising at least one optical element in a beam path of a microscope between an objective lens of the microscope and in front of an eye to be monitored, comprises: (a) a connection device, by means of which the positioning unit can be coupled to the microscope, wherein the positioning unit comprises (b) a positioning device, by means of which the optical element is movable relative to the microscope in the longitudinal direction of the beam path, wherein the positioning device is formed of a first double rocker mechanism and a second double rocker mechanism, wherein the double rocker mechanisms are interconnected by means of a common coupling member. A movability of the optical element in the longitudinal direction of the beam path makes it possible to adjust the optical unit to the eye to be monitored, and/or to adjust the beam path of the microscope to an intermediate image located in the beam path without having to make these adjustments on the microscope. The double rocker mechanisms are preferably each formed of two rod-like rockers, which are each connected, in turn, at their ends to a pivot bearing. A movement of the first double rocker with the coupling member in a circular arc-shaped manner is thus enabled, wherein the second double rocker can likewise move in a circular arc-shaped manner in the same direction, in such a way that a linear movement in the longitudinal direction of the beam path is produced from both circular arc-shaped movements. Owing to this combination of two double rocker mechanisms, it is possible to dispense completely with a linear guide for moving the optical element. The double rocker mechanisms may be formed with single pivot points, or pivot bearings, which are substantially easier to sterilise or seal compared to linear guides. In addition, no specific maintenance or lubrication of the double rocker mechanisms is required, and there is no need to produce specific guides having correspondingly narrow tolerances. The rockers of the double rocker mechanisms, as well as the coupling member, can be produced in this instance from a plastics material, for example. It is also conceivable to form the pivot bearing, required for the connection, of plastics material. On the whole, a production cost for the positioning unit can thus be considerably reduced.

If the positioning unit is formed at least in part of plastics material, then the production costs for the positioning unit can be reduced considerably. Essential components of the positioning unit, which are absolutely necessary for mechanical function, can thus be produced in a cost-effective manner, for example, in an injection moulding process. The cost saving then, attainable by the use of plastics material, makes it possible to dispense completely with a reuse of the positioning unit, and to dispose of the positioning unit after one use. Further cost advantages are thus provided, since no costs are incurred for preparation and maintenance. Owing to the disposable use of the positioning unit thus enabled, contamination risks associated with the sterilisation process and possible defects in the positioning unit can also be excluded. As many components of the positioning unit as possible, as well as components which are expensive to produce, can thus be formed from one plastics material. The positioning unit can thus be designed in the manner of a sterile disposable article, which can be supplied in a protective packaging. Since a reuse or sterilisation of the positioning unit then no longer has to be considered, a particularly cost-effective plastics material may be used. A positioning unit designed in such a way can also be used, in particular, if owing to specific hygiene provisions, a use of re-sterilised instruments is forbidden. There are also then no waiting times for eye operations as a result of instruments undergoing the sterilisation process.

In order to ensure a reliable guide of the optical element in the longitudinal direction of the beam path, the first double rocker mechanism can be connected to the second double rocker mechanism via a toothed gearing in such a way that a movement of the first double rocker mechanism can be transferred to the second double rocker mechanism by means of the toothed gearing. To form the toothed gearing, it may be sufficient for at least one tooth of one of the double rocker mechanisms to be engaged with a tooth pair of the other double rocker mechanism. The respective teeth can be formed in the extension of a rocker of the double rocker mechanisms. The toothed gearing and, therefore, a coupling of movement between the two double rocker mechanisms can thus be produced in a particularly simple and cost-effective manner. If the rockers of the double rocker mechanisms are formed of plastics material, then the toothed gearing may easily be moulded integrally on the respective rockers.

In particular, with use of an injection moulding process to produce the double rocker mechanisms, the double rocker mechanisms and the toothed gearing may be formed in one piece. For example, the toothed gearing may be formed between two rockers, which form the necessary teeth in each case. The teeth may be moulded integrally on the rockers, or formed by an extension of ends of the rockers. A one-piece design may be facilitated, in particular, since the double rocker mechanisms and the toothed gearing are formed basically in a two-dimensional plane. Such plastics material parts can be produced in an injection moulding process in a particularly simple manner.

It is particularly advantageous if the toothed gearing has a gear ratio of 1:1. A uniform and coincident movement of the double rocker mechanisms can thus be enabled with basically coincident lengths thereof, wherein this movement ensures a linear relative movement of the optical element in the longitudinal direction of the beam path.

Furthermore, a first double rocker of the first double rocker mechanism may be mounted on a connecting bearing member, and a second double rocker of the second double rocker mechanism may be mounted on a receiving bearing member. The connecting bearing member and the receiving bearing member may thus interconnect each of the two rockers of the double rocker mechanisms at a defined distance. The connecting bearing member may thus be provided for rigid fastening in the area of the microscope, wherein the coupling member is movable relative to the connecting bearing member, and the receiving bearing member is movable relative to the coupling member and to the connecting bearing member. The optical element and the optical unit may thus be provided in the area of the receiving bearing member. Both the connecting bearing member and the receiving bearing member may be formed from a plastics material, similarly to the double rockers and the coupling member.

In order to move the optical element relatively along the beam path, the positioning device may comprise an adjustment means, by means of which a position of the optical element is adjustable. It can thus be ensured that the optical element is located in the desired position in each case, wherein the adjustment or positioning of the optical element may take place manually, for example, by an operator.

The adjustment means may be formed, for example, of at least one adjusting wheel having a worm gear or an eccentric gear. In one embodiment, the adjusting wheel can thus be mounted on the connecting bearing member and may act on a rocker of the first or second double rocker mechanism by means of a screw moulded integrally on the adjusting wheel. A rotation of the adjusting wheel then changes the distance of the rocker relative to the adjusting wheel depending on which area of the screw is engaged with the rocker. The resultant movement of the rocker consequently leads to a movement of both double rocker mechanisms and, therefore, to a longitudinal movement of the optical element. Such an adjustment means may also be produced from a plastics material in a particularly simple manner. For example, the adjusting wheel with the screw can be produced as an injection-moulded part, which can be easily fitted on a hub. In order to enable operation on either side, two mutually opposed adjusting wheels may also be provided.

To protect an eye against an accidental collision with the optical element, the positioning device may form a safety means that allows a loose movement of the optical element if a force is exerted on the optical element in the direction of the microscope. This means that the positioning device, or safety means, can be formed in such a way that, in the event of an exertion of force on the optical element, for example, caused by a collision with the eye in question, the optical element can be moved, essentially without resistance, in the direction of the objective lens. The safety means may thus be formed in such a way that the positioning device and the optical unit, owing to their respective inherent weight, hold the optical element in a lower position in the vicinity of the eye. If a force is then applied to the optical element in the direction of the microscope, merely a weight of the optical unit and positioning device is to be overcome to move the optical element. In particular, by use of the double rocker mechanisms, a jamming of the safety means in relation to a linear guide can thus be prevented. Furthermore, with a use of plastics material for the relevant components, a weight thereof is comparatively low so that only a small force has to be applied to move the optical element. If the weight is reduced to such an extent that an undesired movement of the optical element can also no longer be excluded, a spring may be provided on the positioning device to stabilise the optical element and applies an additional force in the direction of the eye.

The positioning unit may advantageously comprise an alternating device, by means of which the optical element can be moved into and out of the beam path. The alternating device may be formed in such a way that the optical element can be slid or pivoted into the beam path. The optical element may preferably be pivoted about an axis extending transverse to the beam path, together with the positioning unit. It can thus be ensured that, during an operation, the positioning unit and the optical unit do not restrict or impair a view in an area of movement of the person carrying out the operation above the eye in question. It is thus also possible to move the optical element into and out of the beam path in a simple manner as required.

The alternating device may be formed by the connection device and the positioning device in such a way that the positioning device is pivotable relative to the connection device. Alternatively, the positioning device may be connected directly to the connection device so that it can be moved or pivoted relative to the connection device. Additional components are not necessarily required to form such an alternating device.

The connection device may also be formed of a plastics material. The connection device may be formed so as to be directly rigidly connectable to the microscope or alternatively with an adapter means, which is in turn connected rigidly to the microscope. In this case, the connection device may be connected to the adapter means, for example, in the manner of a plug-in connection, without the aid of an additional tool. If an adapter means is provided on the microscope, this may of course also be formed of a plastics material.

The alternating device can be produced in a particularly simple manner if the alternating device is formed as a hinge, wherein the alternating device may comprise at least one snap-in means, by means of which the optical element is adjustable in a use position in the beam path and/or in an idle position outside the beam path. The hinge may be formed between the connection device and the positioning device so that it is possible to pivot the positioning device relative to the connection device. Furthermore, the snap-in means may be formed on the connection device and the positioning device and may, in turn, be formed of a locking lug and locking indentations for engagement with the locking lug. The locking lug and the locking indentations may each be moulded integrally on the connection device or the positioning device. The locking indentations may be arranged so that the locking lug engages in a locking indentation both in the use position and in the idle position, and the optical element and the positioning device can thus be locked in place.

Pivot bearings or link brackets of the double rocker mechanisms can be formed in a particularly simple manner by a living hinge in each case. In particular, if the double rocker mechanisms are formed completely of plastics material, then this is particularly advantageous, since all components of the double rocker mechanisms can thus be produced in an injection moulding process together with the link brackets moulded integrally thereon. Furthermore, the assembly of the double rocker mechanisms, which is otherwise necessary, can thus also be dispensed with completely.

The positioning unit can be produced in a particularly cost-effective and simple manner if the positioning unit is formed completely of plastics material. The positioning unit may be formed of only a few components since it is possible, for example, in a plastics injection moulding process, to also produce spatially complex components that could only be produced from metal at high cost. For example, a polyamide may be used as a plastics material, in particular, owing to its mechanical properties. It is thus also possible, after use, to feed the entire positioning unit to a contaminated special waste at no further cost.

The monitoring device, according to the invention, comprises a positioning unit according to the invention and at least one optical unit, wherein the optical unit comprises at least one optical element. The optical unit is thus a component of the monitoring device, which may comprise a plurality of optical units in alternative embodiments. The optical unit also comprises at least one optical element, such as a lens or a prism, wherein a plurality of optical elements may also be provided, which form a group of lenses or prisms of the optical unit. With regard to the advantages of the monitoring device according to the invention, reference is made to the above descriptions of features of the positioning unit.

In order to form an easily operable connection between the positioning unit and the optical unit, the positioning unit may comprise a receiving device, by means of which the optical unit can be adapted to the positioning unit, wherein the optical unit may form a holding means for holding the optical element and connecting it to the receiving device. The receiving device makes it possible to form the optical unit separately from the positioning unit and, if required, to exchange the optical unit during an eye operation, for example, without having to replace the entire positioning unit. It is thus still down to the person carrying out the operation to supplement, as required, the positioning unit with the optical unit to form the monitoring device. In order to enable a standardised connection between the optical unit and the receiving device, the optical element(s) can be held by the holding means in the provided position, wherein the holding means may be formed connected to the receiving device of the positioning unit, for example, in the manner of a plug-in connection. Owing to this interface on the positioning unit, conventional optical units can also be adapted to the positioning unit.

Alternatively, the positioning unit may form a holding means for holding the optical element. Consequently, the optical element may be held directly by the positioning unit without having to form a receiving device on the positioning unit. In particular, if the positioning unit is formed of plastics material, the holding means can be moulded integrally on the positioning device so that, in order to assemble the optical element, this only has to be inserted into the holding means.

To ensure singular use of the monitoring device, the holding means, and/or the receiving device, and/or a connection device may comprise at least one connecting element that is formed in such a way that it is destroyed upon separation of the holding means and receiving device and/or connection device and a microscope. In particular, if components made of plastics material are used to form the monitoring device, a sterilisation of the monitoring device or of the plastics material components is not possible and is also undesirable. It is consequently to be ensured that these components are not reused in further eye operations. A connecting element may, therefore, be provided on the holding means, the receiving device, or the connection device and is formed, for example, in the manner of a snap-in element that has an intended breaking point and that locks in place upon assembly of the components in such a way that disassembly is only possible with forcible destruction of the connecting element. Renewed assembly and use is thus made difficult or impossible. The destroyed connecting element, or the relevant component, can also be recognised by a user as already having been used and, therefore, as being unusable.

The monitoring device can also be produced in a yet more cost-effective manner if the optical unit is formed of plastics material. One or more optical elements of the optical unit can also be produced from plastics material of corresponding optical quality.

The optical unit may also be formed in one piece, in particular, if the holding means is formed of the same material as the optical element. The optical element may then be formed together with the holding means in an injection moulding or pressing process. The optical unit may, therefore, also be produced so cost effectively that a reuse thereof can be omitted.

The optical element may be formed as an ophthalmoscopy lens, which is used to monitor an ocular fundus.

The optical element may also be formed as a reducing lens, which is used to adjust the beam path. The monitoring device may also comprise merely an ophthalmoscopy lens, or an ophthalmoscopy lens with a reducing lens as a further optical element of a further optical unit. Additional optical units for image reversal and/or exchange of two beam paths may thus also be provided. When using a plurality of optical units, it is also possible to combine on the positioning unit reusable, sterilisable optical units with non-reusable optical units made of plastics material.

Further advantageous embodiments of the monitoring device, according to the present invention, will become clear from the descriptions of features of the various relevant embodiments that refer back to the device according to the first embodiment mentioned above.

BRIEF DESCRIPTION OF THE DRAWINGS

Preferred embodiments of the invention will be described hereinafter in greater detail with reference to the accompanying drawings, in which.

DETAILED DESCRIPTION OF THE INVENTION

A monitoring device 10 comprising a positioning means 11 in various representations and positions can be derived by comparing FIGS. 1 to 5. The monitoring device 10 comprises optical units 12 and 13, wherein the optical unit 12 is only illustrated in part in this instance. Merely an annular holding means 14 of the optical unit 12, which annular holding means 14 is used to receive a reducing lens (not shown here) is illustrated in this instance. The optical unit 13 is formed by an ophthalmoscopy lens 15 and a holding means 16. The holding means 16 comprises a mount 17 for holding the ophthalmoscopy lens 15 and an angular holder 18 for connection to a receiving device 19 of the positioning means 11. The reducing lens (not shown in this instance) and the ophthalmoscopy lens 15 may be arranged in a beam path 20, illustrated suggestively in this instance, of a microscope (not shown in this instance than its beam path 20).

Figure 1:
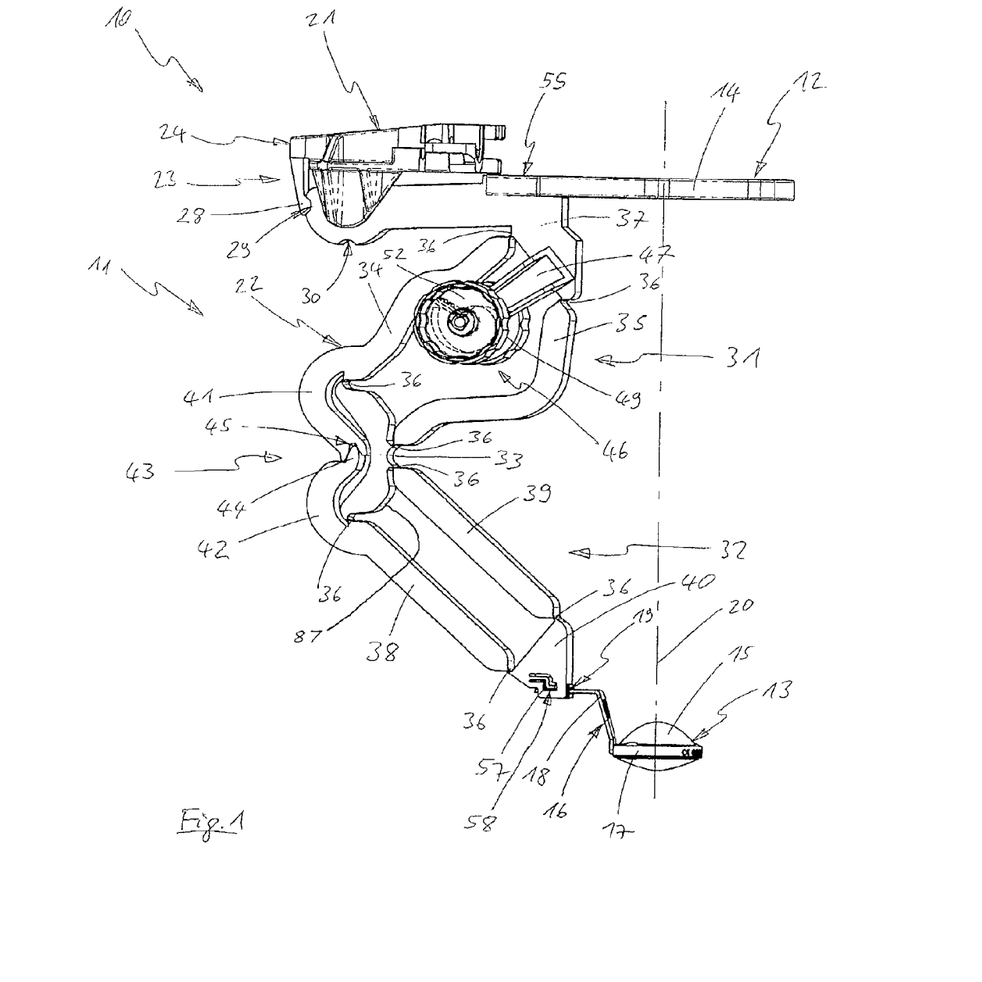
FIG. 1 is a perspective view of a monitoring device, according to the present invention, comprising a positioning unit in a lower working position.
Figure 5:
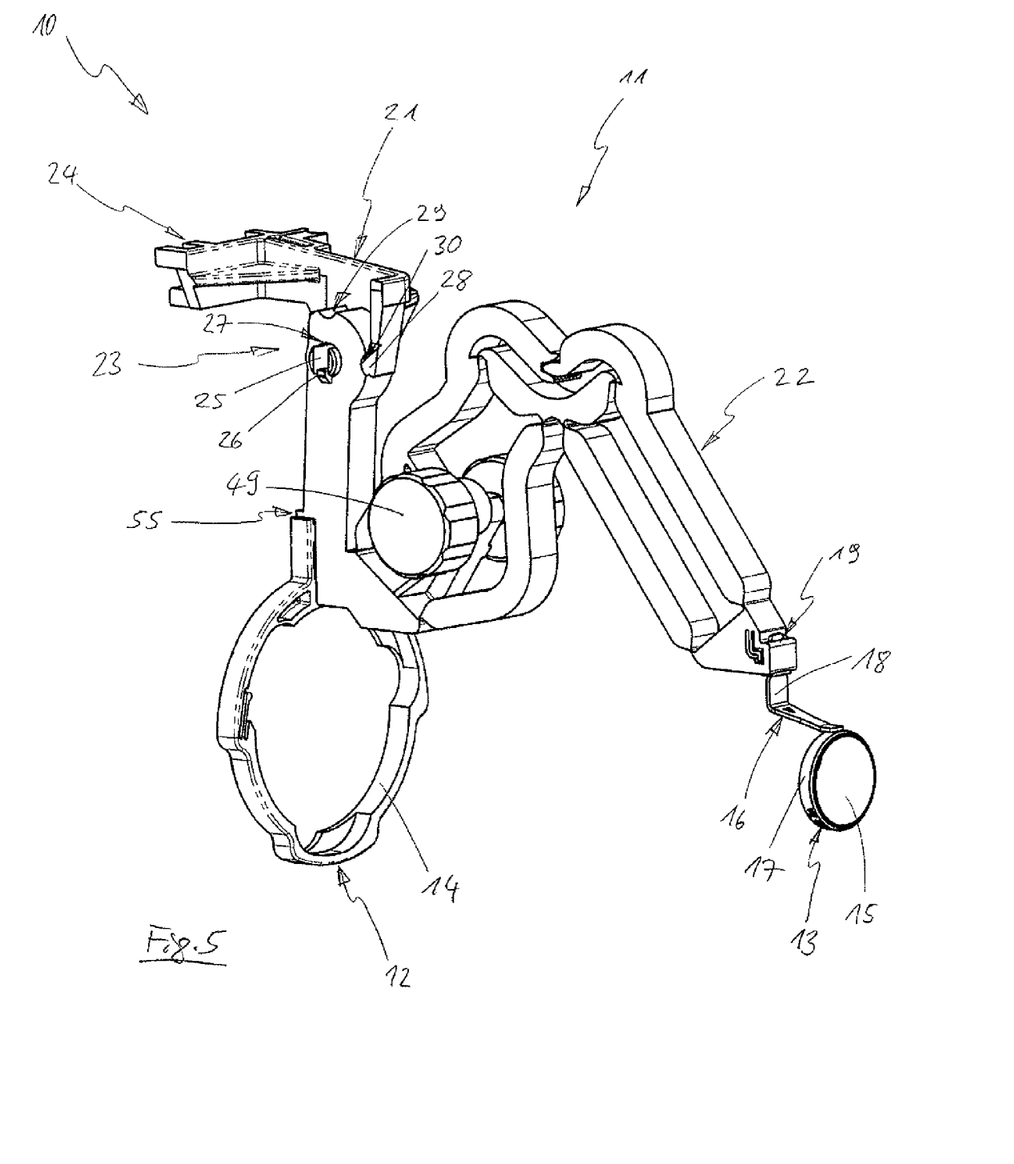
FIG. 5 is a perspective view of the monitoring device from FIG. 1 in an idle position.

The positioning unit 11 comprises a connection device 21 and a positioning device 22, wherein an alternating device 23 for pivoting the positioning device 22 with the optical units 12 and 13 out of and into the beam path 20 is formed between the connection device 21 and the positioning device 22, as can be seen by comparing FIGS. 1 and 5. The connection device 21 consists of a plastics material and is produced in one piece by an injection moulding process. Engagement elements 24 for connecting the connection device 21 to an adapter means or device (not shown in this instance) of a microscope are formed on the connection device 21. The connection device 21 further forms a shaft 25 having a locking lug 26, which can be inserted into a hub 27 of the positioning device 22 and can be locked in place as illustrated. The positioning device 22 can thus now be pivoted about the shaft 25. In addition, a further locking lug 28 is formed on the connection device 21 and can engage in locking indentations 29 and 30 in the positioning device 22. The locking indentations 29 and 30 are formed in the positioning device 22 in such a way that the positioning device 22 can be locked in place in the use position illustrated in FIG. 1, or in the idle position illustrated in FIG. 5 by engagement with the locking lug 28.

The positioning device 22 is formed of a first double rocker mechanism 31 and a second double rocker mechanism 32. The double rocker mechanisms 31 and 32 are interconnected by means of a common coupling member 33. The common coupling member comprises a perimeter 87. The first double rocker mechanism comprises an upper pair of first and second rocker arms 34 and 35, which are each connected via a living hinge 36 to the coupling member 33 and to a connecting bearing member 37. The second double rocker mechanism 32 comprises a lower pair of first and second rocker arms 38 and 39, which are each connected by means of living hinges 36 to the coupling member 33 and to a receiving bearing member 40. The rocker arms 34 and 38, or ends 41 and 42, formed thereon further form a toothed gearing 43 with a tooth 44 and a tooth gap 45. A movement of the rocker arms 34 and 35 thus transfers the movement, by rolling the tooth 44 in the tooth gap 45, to the lower pair of rocker arms 38 and 39 in a gear ratio in this instance of 1:1, and thus moves the ophthalmoscopy lens 15 along the beam path 20 of the microscope.

Figure 2:
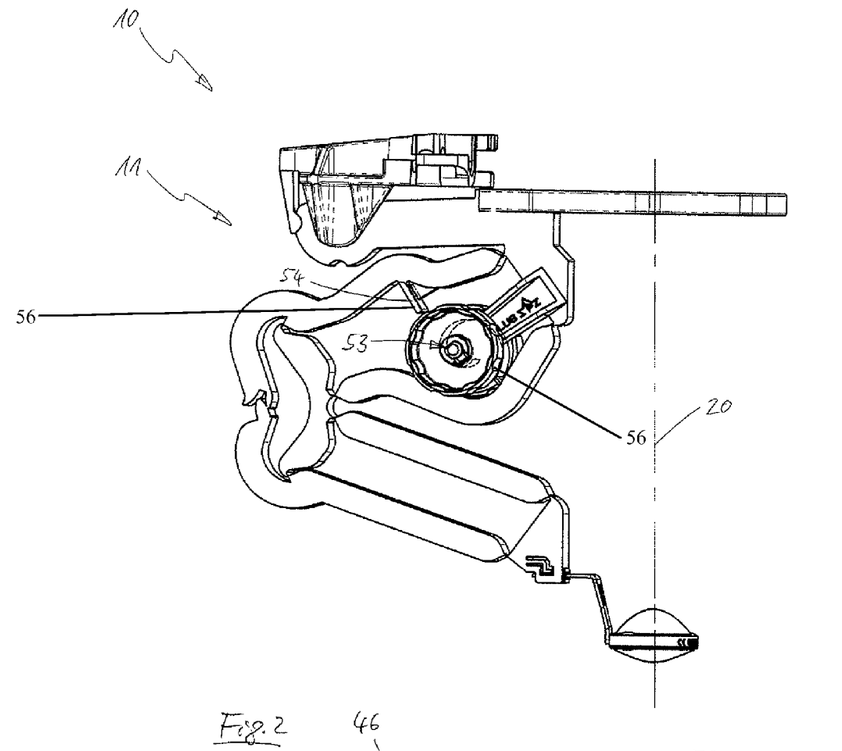
FIG. 2 is a perspective view of the monitoring device of FIG. 1 comprising the positioning unit in an upper working position.
Figure 3:
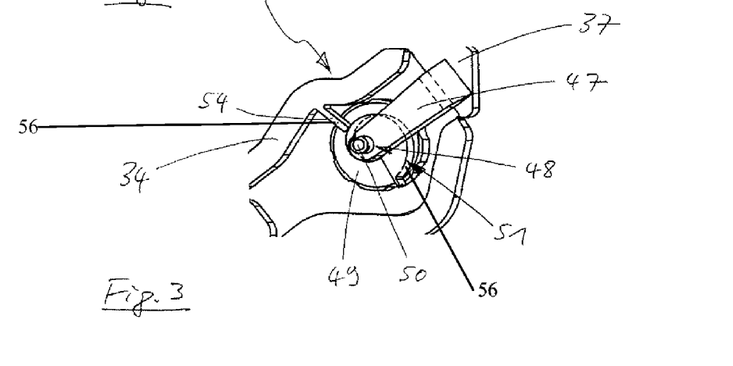
FIG. 3 is a perspective view of a detail of an adjustment means.
Figure 4:
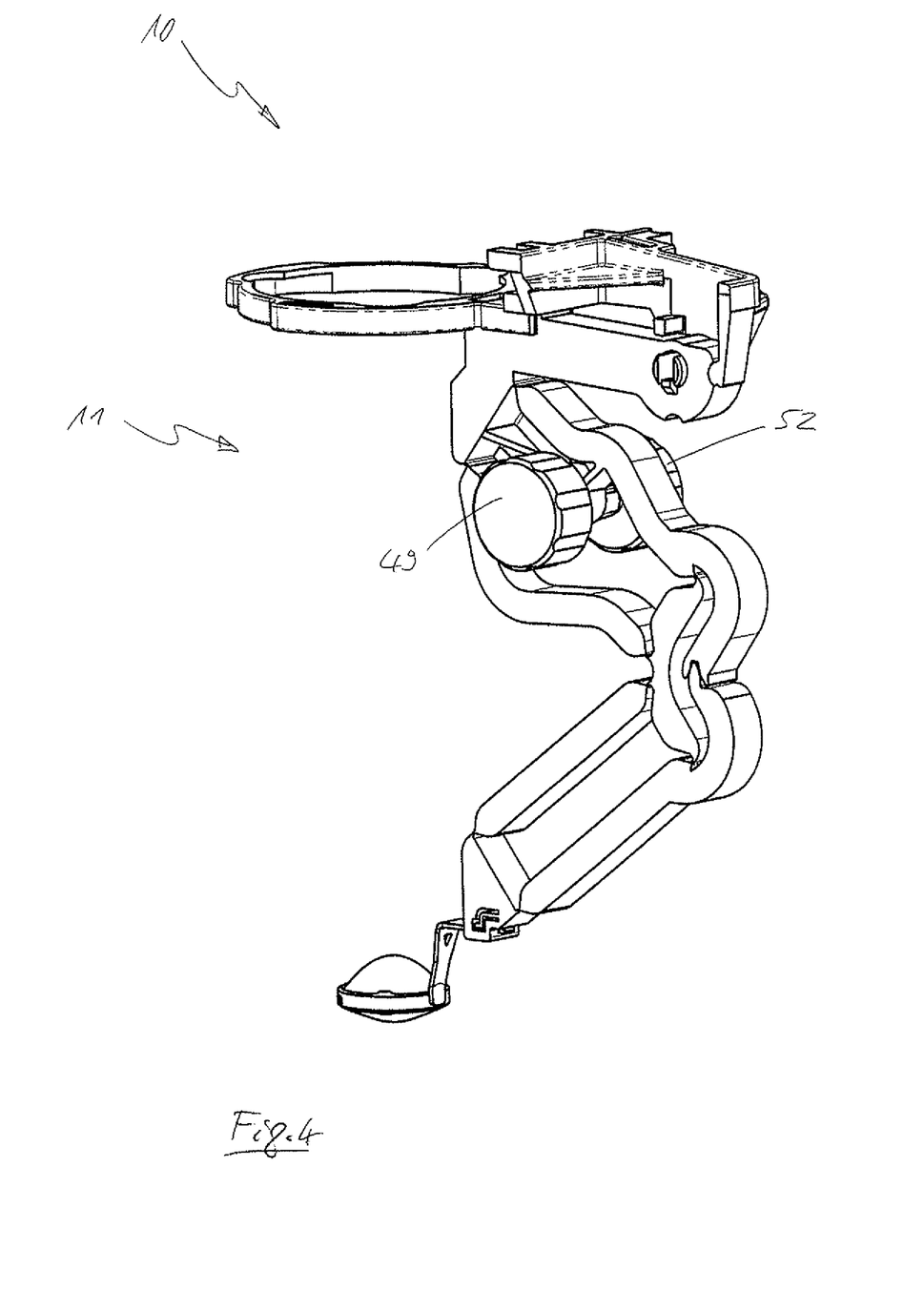
FIG. 4 is a rear, perspective view of the monitoring device from FIG. 1.

The positioning device 22 further comprises an adjustment means 46. As can be seen in greater detail from FIG. 3, the adjustment means 46 is formed of a holding element 47 moulded integrally on the connecting bearing member 37 and having a hub 48. An adjusting wheel 49 having a shaft 50 and a screw curve 51 moulded integrally on the adjusting wheel 49 is fitted on the hub 48. Opposite the adjusting wheel 49, a further adjusting wheel 52 having a hub 53, as can be seen, for example, from FIG. 1, and is fitted on the shaft 50. A rotation of the adjusting wheels 49 or 52 now rolls the screw curve 51 over a cam 54, which is moulded integrally on the rocker arm 34. The rocker arm 34 is thus movable relative to the connecting bearing member 37 so that the ophthalmoscopy lens 15 can be moved, by turning the adjusting wheels 49 and 52, from the lower working position shown in FIG. 1 into the upper working position shown in FIG. 2. The screw curve 51, or the adjusting wheel 49, is pressed against the cam 54 by the inherent weight of the double rocker mechanisms 31 and 32 as well as by the inherent weight of the optical unit 13. If a force is exerted on the ophthalmoscopy lens 15 in the direction of the microscope (not shown in this instance in more detail), for example, by accidental contact between the ophthalmoscopy lens 15 and an eye to be operated on, the ophthalmoscopy lens 15, as illustrated in FIG. 2, can be moved into the upper working position against the aforementioned weight without a greater expenditure of force being necessary. The cam 54 can thus be easily removed or lifted off from the screw curve 51 without a further force having to be applied for this purpose. A safety means 56 thus formed may effectively prevent possible damage in the event of a collision with an eye.

In addition, the double rocker mechanisms 31 and 32 are formed in one piece together with the holding element 47 from a plastics material. The adjusting wheels 49 and 52 are each also formed of a plastics material. It is thus possible to produce the positioning unit 11 from merely four components that are made of plastics material and can be easily plugged together. The holding means 14 is also formed of plastics material, wherein the holding means 16 consists of metal and is provided for sterilisation and reuse. The positioning device 22 further comprises a second receiving device 55 on the connecting bearing member 37, on which the annular holding means 14 can be fitted. Alternatively, it is possible to also use a holding means (not shown in this instance) and ophthalmoscopy lens made of plastics material. In order to ensure a secure hold of the holding means 16 in the receiving device 19, the receiving device 19 formed in the receiving bearing member 40 comprises two spring elements 57, which are each formed by a recess 58 and can be engaged with undercuts (not shown in this instance) in the holder 18. The spring elements 57 press from above onto the holder 18. The spring elements 57 are formed in such a way that they are destroyed when the holder 18 is removed from the receiving device 19. Only one individual spring element may also optionally be formed. It is thus clear to a user that the positioning unit 11 has already been used and cannot be reused.

Figure 6:
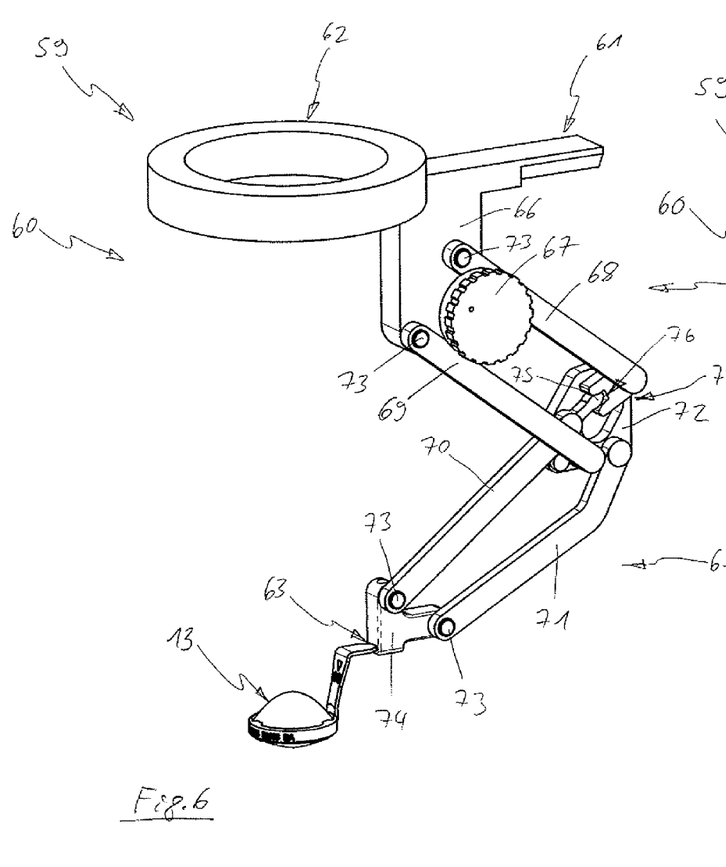
FIG. 6 is a perspective view of a further monitoring device, according to the present invention, comprising a positioning unit.
Figure 7:
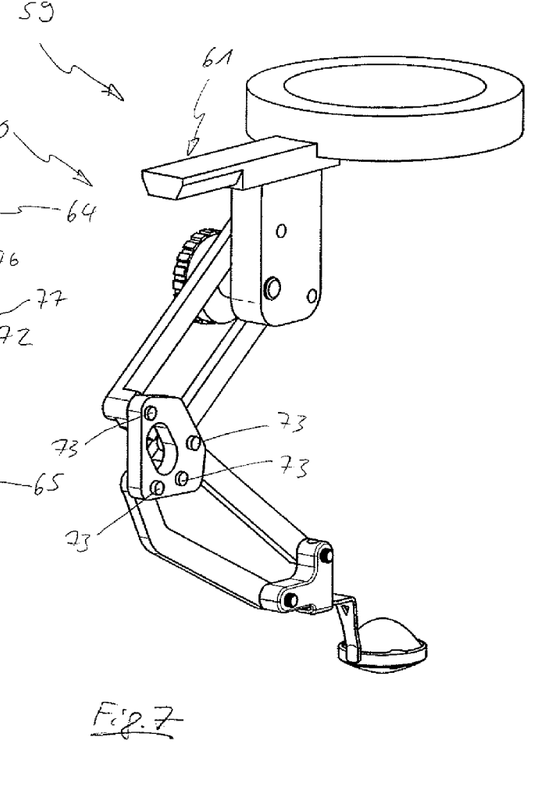
FIG. 7 is a rear view of the monitoring device from FIG. 6.

If FIGS. 6 and 7 are compared, a further embodiment of a monitoring device 59 comprising a positioning unit 60 and a connection device 61 on the positioning unit 60 is shown. A holding means 62 for receiving a reducing lens (not shown in this instance) is formed on the positioning unit 60. An optical unit 13, as illustrated in FIGS. 1 to 5, is also fitted on a connection device 63 of the positioning unit 60. In contrast to the positioning unit illustrated in FIGS. 1 to 5, in this case, a first double rocker mechanism 64 and a second double rocker mechanism 65 are formed in a number of parts. The first double rocker mechanism 64 comprises a connecting bearing member 66, on which an adjusting wheel 67 is rotatably mounted, and rockers 68 and 69 which, similarly to rockers 70 and 71 of the second double rocker mechanism 65, are mounted rotatably on a coupling member 72 via pin connections 73 in each case. The rockers 70 and 71 are also connected rotatably to a receiving bearing member via the pin connections 73. A tooth 75 is formed on the rocker 70 and engages in a tooth gap 76 of the rocker 68 and thus forms a toothed gearing 77. A function of the double rocker mechanisms 64 and 65 with the adjusting wheel 67 basically corresponds to the previously described function of the positioning unit from FIGS. 1 to 5. Owing to the simple shape of the components, the positioning unit 60 can also easily be formed of metal in a cost-effective manner, wherein, in this instance, too, the positioning unit 60 is formed predominantly of plastics material.

The invention claimed is:

1. A positioning unit for positioning an optical unit comprising at least one optical element in a beam path of a microscope between an objective lens of the microscope and in front of an eye to be monitored, wherein the positioning unit comprises:
   (a) a connection device, wherein the connection device couples the positioning unit to the microscope; and
   (b) a positioning device, wherein the positioning device comprises an upper pair of first and second rocker arms and a lower pair of first and second rocker arms, and a common coupling member, the common coupling member comprises a perimeter thereof, wherein upper and lower pairs of first and second rocker arms are each directly connected by a link bracket to the perimeter of the common coupling member such that the upper and lower pairs of first and second rocker arms are connected at four different points to the perimeter of the common coupling member, wherein each link bracket pivots about the point of contact with the perimeter of the common coupling member, wherein the upper first rocker arm is connected directly to the lower first rocker arm via a toothed gearing so that movement of the upper first rocker arm is transferred to the lower first rocker arm via the toothed gearing, and wherein the toothed gearing is separate from the common coupling member such that the first upper and lower rocker arms are both directly connected to the common coupling member and to each other via the toothed gear.

2. The positioning unit according to claim 1, wherein the upper and lower first rocker arms and the toothed gearing are formed together in one piece.

3. The positioning unit according to claim 1, wherein the toothed gearing has a gear ratio of 1:1.

4. The positioning unit according to claim 1, wherein the upper first and second rocker arms are attached to a connecting bearing member, and the lower first and second rocker arms are attached to a receiving bearing member.

5. The positioning unit according to claim 1, wherein the positioning device further comprises:
   (c) an adjustment means that adjusts a position of the optical element.

6. The positioning unit according to claim 5, wherein the adjustment means comprises at least one adjusting wheel having a worm gear or an eccentric gear.

7. The positioning unit according to claim 1, wherein the positioning device forms a safety means that allows a loose movement of the optical element when a force is exerted on the optical element in a direction of the microscope.

8. The positioning unit according to claim 1, wherein the positioning unit further comprises:
(c) an alternating device that moves the optical element into and out of the beam path.

9. The positioning unit according to claim 8, wherein the alternating device includes the connection device and the positioning device so that the positioning device is pivotable relative to the connection device.

10. The positioning unit according to claim 8, wherein the alternating device comprises a hinge and at least one snap-in means, wherein the at least one snap-in means is operable to lock the optical element in a use position in the beam path, or in an idle position outside the beam path, or the at least one snap-in means is operable to lock the optical element in both the use position in the beam path and in the idle position outside the beam path.

11. The positioning unit according to claim 1, wherein link brackets comprise, in each case, a living hinge.

12. The positioning unit according to claim 1, wherein the positioning unit is formed completely of plastics material.

13. A monitoring device comprising
i. a positioning unit according to claim 1; and
ii. at least one optical unit, wherein the optical unit comprises at least one optical element.

14. The monitoring device according to claim 13, wherein the positioning unit further comprises:
(c) a receiving device, wherein the receiving device adapts the optical unit to the positioning unit, and wherein the optical unit includes a holding means arranged to hold the optical element and connecting the optical element to the receiving device.

15. The monitoring device according to claim 13, wherein the positioning unit comprises a holding means arranged to hold the optical element.

16. The positioning unit according to claim 1, wherein the upper and lower first rocker arms and the toothed gearing are formed together in one piece.

17. The monitoring device according to claim 14, wherein the connection device comprises at least one connecting element, which is formed in such a way that the at least one connecting element is destroyed upon separation of the connection device and the microscope.

18. A positioning unit for positioning an optical unit comprising at least one optical element in a beam path of a microscope between an objective lens of the microscope and in front of an eye to be monitored, wherein the positioning unit comprises:
(a) a connection device, wherein the connection device couples the positioning unit to the microscope; and
(b) a positioning device, wherein the positioning device moves the optical element relative to the microscope in a longitudinal direction of the beam path, wherein the positioning device comprises an upper pair of first and second rocker arms and a lower pair of first and second rocker arms, and a common coupling member, the common coupling member comprises a perimeter thereof, wherein upper and lower pairs of first and second rocker arms are each directly connected by a living hinge to the perimeter of the common coupling member such that four living hinges in total are used to connect the upper and lower pairs of rocker arms to the common coupler, wherein the upper first rocker arm is connected directly to the lower first rocker arm via a toothed gearing so that movement of the upper first rocker arm is transferred to the lower first rocker arm via the toothed gearing, and wherein the toothed gearing is separate from the common coupling member such that the first upper and lower rocker arms are both directly connected to the common coupling member and to each other via the toothed gear thereby providing five pivot points represented by the four living hinges and the toothed gear.

* * * * *